United States Patent [19]

Fanselow et al.

[11] Patent Number: 4,476,593
[45] Date of Patent: Oct. 16, 1984

[54] TANNING BLANKET

[75] Inventors: Dan L. Fanselow, White Bear Lake; Sanford Cobb, Jr., St. Marys Point; Ronald E. Bergsten, Spring Lake Park, all of Minn.

[73] Assignee: Minnesota Mining and Manufacturing Company, St. Paul, Minn.

[21] Appl. No.: 406,353

[22] Filed: Aug. 9, 1982

[51] Int. Cl.³ .......................... B32B 3/26; B32B 3/30
[52] U.S. Cl. ........................................ 5/417; 5/421; 428/161; 428/172; 428/461; 428/913
[58] Field of Search ............... 428/148, 161, 172, 458, 428/461, 913, 542; 5/417-420, 421

[56] References Cited

FOREIGN PATENT DOCUMENTS 2431271  3/1980  France ................................ 5/417
2475400  8/1981  France ................................ 5/417
2481588 11/1981  France ................................ 5/417

*Primary Examiner*—Paul J. Thibodeau
*Attorney, Agent, or Firm*—Donald M. Sell; James A. Smith; Edward T. Okubo

[57] ABSTRACT

A tanning blanket for reflecting a large portion of the solar radiation which is otherwise scattered in directions away from the person using the blanket, towards the flanks of the person, the blanket having a plurality of incremental reflectors in a Fresnel pattern on a flexible substrate, which reflectors reflect incident solar radiation toward the person and distribute the reflected radiation across the flanks of the person.

7 Claims, 4 Drawing Figures

TANNING BLANKET

BACKGROUND OF THE INVENTION

This invention relates to a tanning blanket for reflecting solar radiation which would not otherwise be incident upon a person, toward the person occupying the blanket.

There are at present a number of devices being sold which attempt to reflect otherwise non-incident solar radiation toward a person for the purpose of expediting or more efficiently utilizing the sun's natural tanning process for that person. One such device is a flexible mat formed from a dimpled plastic sheet which has been vapor coated with aluminum. Another device is an inflatable air mattress which is adapted for tanning purposes by having a clear plastic top layer and a reflectorized surface on the inside of the lower layer. Neither of these devices however, effectively augments the amount of solar radiation which is ultimately directed toward the person.

SUMMARY OF THE INVENTION

In view of this shortcoming of the aforementioned devices, the tanning blanket of the present invention is an improvement in that a large portion of the solar radiation which is otherwise scattered in directions away from the person, is not only reflected and directed toward the person using the blanket but also distributed across the flanks of the person in order to produce a more even sun tan. This is accomplished through the use of a plurality of oriented flexible incremental reflectors within the blanket. The tanning blanket comprises a flexible substrate including a plurality of elongate facets having a reflective covering thereon. These facets are obliquely oriented to direct incident solar radiation generally toward a focal axis located a predetermined distance above the blanket and approximately mid-way between two opposing outer edges of the blanket. The actual angle that the facets make with respect to the horizontal surface upon which the blanket is placed (or in effect with respect to the imaginary base line which would be created if the ends of adjacent facets, that are most distant from the outer edge of the blanket, were interconnected) is chosen to optimize the reflective efficiency of the incremental reflectors in order to direct a greater portion of the solar radiation toward the person, which radiation might otherwise be dispersed away from the person.

To further optimize the reflection efficiency of the blanket and also prevent destruction of the reflectorized surface of the blanket or degradation of its reflective efficiency through such things as an accumulation of dirt between the facets, the present invention also contemplates the addition of a top layer to the blanket, which covers and protects the reflective surface, and in so doing, refracts the reflected radiation at an even lower angle with respect to the person. This top layer can also be made wavelength selective, to afford a blanket which can selectively absorb radiation in the sun burning spectral range, thus continuing to promote sun tanning while minimizing sun burning.

BRIEF DESCRIPTION OF THE DRAWINGS

The present invention will be further described hereinafter with reference to the accompanying drawing wherein.

DETAILED DESCRIPTION

Figure 1:
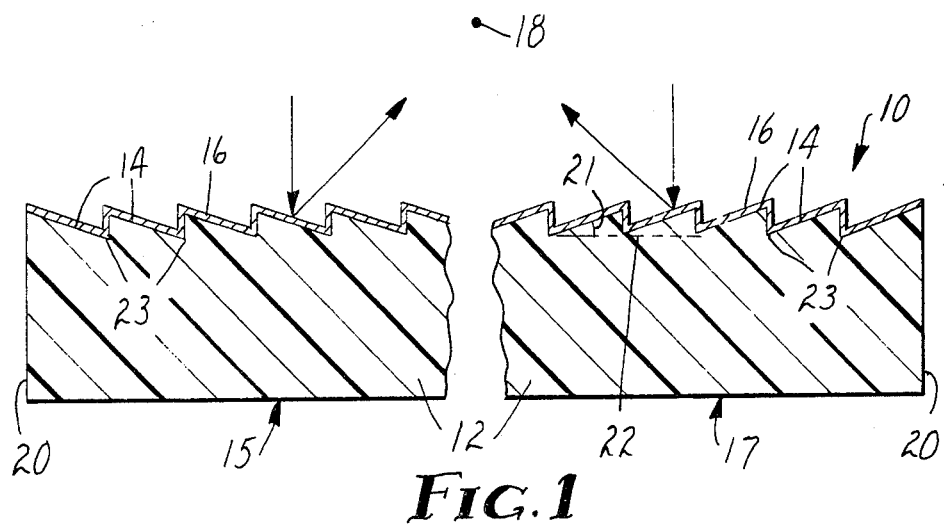
FIG. 1 is a partial transverse sectional view of the blanket according to the present invention.

A first embodiment of the tanning blanket 10 according to the present invention is illustrated in FIG. 1. This tanning blanket 10 comprises a flexible substrate 12 including a plurality of elongate facets 14 having a reflective covering 16 thereon. These facets 14 are obliquely oriented to direct incident solar radiation generally toward a focal axis 18 located a predetermined distance above the blanket 10 and approximately mid-way between two opposing outer edges 20 of the blanket 10. The blanket 10 typically has at least two generally symmetric portions, 15 and 17, with each portion having its facets 14 oriented to reflect incident solar radiation away from the outer edge 20 of that particular portion and toward the center of the blanket 10.

To make the blanket 10 more efficient it is desirable to vary the angle 21 of adjacent facets 14 across the width of the blanket 10, so as to provide at least some concentration of the reflected radiation. This angle 21 can be measured with respect to the horizontal under-surface of the blanket 10, or in other words, with respect to an imaginary base line 22 which would be defined by a line interconnecting the ends 33 of adjacent facets, which ends 23 are most distant from the outer edge 20 of the blanket 10. In the embodiment illustrated in FIG. 1 the facets which are farthest from the outer edges 20 of the blanket 10, i.e., closest to the focal axis 18, are formed with an angle 21 equalling 22°. This angle 21 is progressively increased for each successive facet toward the outer edges 20 of the blanket 10, with the facet 14 closest to the outer edge 20 having an angle 21 of approximately 39°. This outer facet on the outer edge 20 of the blanket 10 will generally be approximately 12 inches (30.5 cm) from the flanks of the body of the person utilizing the blanket 10. The progressive increase in the angle 21 toward the outer edges of the blanket 10 causes a greater percentage of the radiation which is incident on the blanket 10 to be directed or reflected toward the focal axis 18 and thus toward the flanks of the person utilizing the blanket 10, thereby increasing the blanket's reflection efficiency.

Typically the structure as thus far described, is achieved by forming the flexible substrate 12 from a polymeric substance such as an acrylate, polycarbonate, polypropylene or vinyl, etc. Although these substances may differ in their chemical and physical properties, they share the characteristic that they are easily impressioned or engraved with facets 14. In the example described, a 0.032 inch (0.8 mm) thick film of clear acrylate, such as that available from Rohm and Haas, Inc. under the designation DR61, was utilized. This film was thermally embossed in a platen press such that one side of the film received specially designed facets 14 in an incremental lens or Fresnel pattern, from a nickel electroformed stamper (which has not been illustrated) within the press. Such a manufacturing technique for Fresnel lenses is well known. It should, however, be pointed out that other engraving and etching techniques might also be used to obtain such a Fresnel pattern. This Fresnel pattern was then vapor deposited with a 1,000 Å coating 16 of aluminum, turning the facets 14 into incremental reflectors. Other reflective coatings, such as tin oxide, could also have been utilized.

Figure 2:
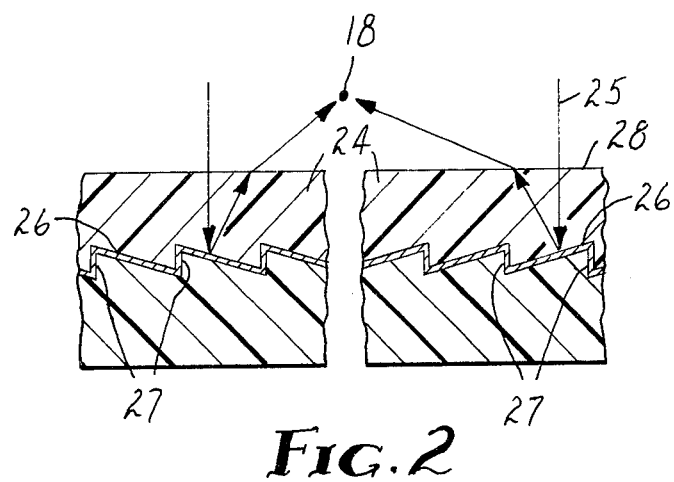
FIG. 2 is a partial transverse sectional view of a second embodiment according to the present invention.

Although this incremental reflector structure can be utilized, as is, for a tanning blanket, its performance can be further improved by covering the aluminum coated facets with a cover layer 24 that is transparent to ultraviolet radiation (see FIG. 2). This cover layer 24 must be in continuous and intimate contact with the aluminum coated facets 26 in order to achieve the desired result. As can be seen, the incoming radiation 25 is reflected from the metallized facets 26 through the cover layer 24. The reflected radiation is also refracted at the cover layer-air interface 28 to exit at an even lower angle and in a direction toward the center of the blanket. This transparent cover layer construction is known as a second surface reflector. There are at least two advantages in utilizing a second surface reflector. First, it is possible to achieve a higher reflection efficiency at the low exit angles required to reach sites immediately above the blanket, as for example to reach the lower portions of the flanks of a person who is lying on the blanket. Second surface reflectors also permit the use of lower reflecting facet angles while still achieving the necessary lower exit angles. Consequently, there are lower losses due to internal reflection from the vertical risers 27 which interconnect adjacent facets. This is particularly important at portions of the blanket most remote or distant from the body, i.e., at the outer edges of the blanket, where the facet angles are necessarily the greatest. This cover layer or surface also protects the metallized reflector surface and minimizes or prevents its physical destruction due to scratching or the accumulation of dirt or other opaque particles within the grooves.

Experiments were conducted in sunlight to compare the relative reflection efficiency of a polypropylene top-coated construction according to the present invention, with that of the dimpled aluminized blanket described as prior art. Over multiple trials, the construction of the present invention achieved between two and four times the reflection efficiency of the dimpled aluminum blanket, for the same collector area, at delivering ultraviolet-B to the flanks.

There are several ultraviolet transparent cover layers that could be utilized in forming a second surface reflector. For example, a 1.6 mil (0.04 mm) film of polypropylene can be laminated to the incremental reflector with an appropriate adhesive such as Food Packaging Adhesive No. 125-858, (commercially available from Findley Adhesive of Milwaukee, Wisconsin). It is also possible to cast a polyurethane layer over the metallized incremental reflectors thus forming a cover layer that is a single component.

In a third example (see FIG. 3) a 0.0015 inch (0.04 mm) film of Mylar ® (polyethylene terephthalate) 30 is laminated to the incremental reflector 32 with a copolymer adhesive (not shown) such as 94% isooctylacrylate:6% Acrylamide. The Mylar ® film 30 is similar to the polypropylene film as far as its protective and refractive capabilities. However, Mylar ® is also capable of absorbing ultraviolet radiation wavelengths shorter than 320 nanometers, while transmitting longer wavelengths. Solar radiation is known to contain both midrange ultraviolet-B radiation which is in the 280 to 320 nanometer region and a longer wavelength ultraviolet-A radiation which is in the 320 to 400 nanometer region. Furthermore, it is known that the ultraviolet-B radiation is generally responsible for sunburning and long term tanning while the ultraviolet-A radiation is generally responsible for immediate pigmentation and some long term tanning. Tests conducted between an incremental lens with the polypropylene cover layer as compared to an incremental lens with a Mylar ® film cover layer show the latter affording a substantial reduction in the amount of ultraviolet-B radiation reaching the person with only a minimal reduction in the ultraviolet-A radiation being reflected toward the person. This is because the Mylar ® construction is able to absorb the more erythemogenic ultraviolet-B radiation while being effectively transparent to and reflecting the ultraviolet-A tanning radiation. Thus, this latter construction is able to further enhance the tanning capability of the present invention by reflecting the radiation that is capable of generating tanning, while absorbing the radiation principally responsible for sun burning.

Figure 3:
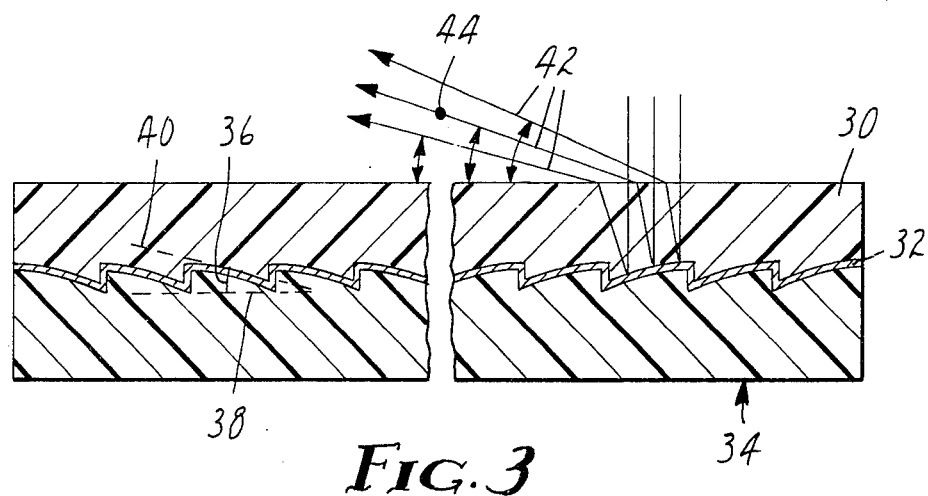
FIG. 3 is a partial transverse sectional view of a third embodiment according to the present invention.

FIG. 3 also shows a tanning blanket 34 wherein the facets 32 are curved to slightly disperse the radiation and thereby produce an even distribution of the tanning radiation in a small area around the focal axis 44. This is the preferred embodiment for the tanning blanket of the present invention. To illustrate this embodiment, a polypropylene-acrylate tanning blanket construction was made by the previously described method. However, the individual facets were constructed with a curvature such that the facet angle at various tangent points across the facet surface varied by ±7.5 degrees. The facet angles 36 (i.e., the angle between the imaginary baseline 38 formed by interconnecting the edges of the adjacent facets, that are most distant from the outer edges of the blanket, and the imaginary facet line formed by a line 40 which is tangent to the curved front surface of the facet at the midpoint of the facet) were varied from an angle of 13.78 degrees at a position 12 inches from the outer edge of the blanket to 19.5 degrees at the outer edge of the blanket. This type of curved facet gives a range of exit angles from the incremental reflector which cover a minimum arc of 40 degrees due to the curvature of the facet. As can be seen, this curvature disperses the reflected and refracted radiation 42 in a small area around the focal axis 44. This slight dispersion minimizes any concentration of the solar radiation which potentially could be injurious to the user, and more evenly distributes the suntanning rays along the flank of a person utilizing the blanket 34.

Figure 4:
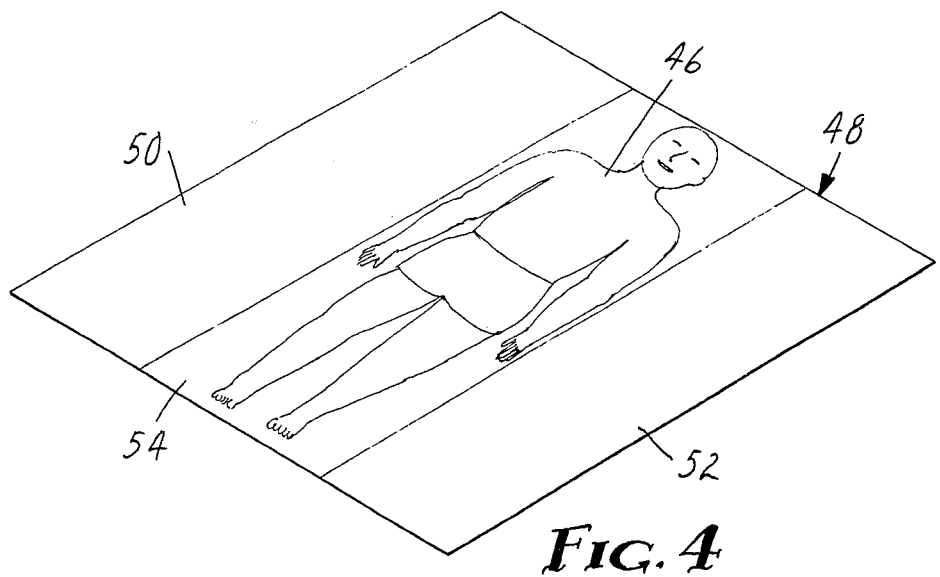
FIG. 4 is a schematic illustration of a blanket according to the present invention being used.

FIG. 4 illustrates a person 46 lying upon a blanket 48 according to the present invention. As can be seen, the blanket 48 has three portions 50, 52, 54. Of these, 50 and 52 have the symmetric flexible incremental reflector structure described above, and portion 54 is a connecting material which need not have the reflector structure since it is largely covered by the person 46 occupying the blanket. Typically the portion 54 can be a beach towel, a non-faceted extension of the flexible substrate forming the reflector, or some similar flexible backing material upon which a person could lie. The reflectorized facets (not shown) within portions 50 and 52, located on either side of the person 46, would be oriented to direct the incident solar radiation toward the flanks of the person 46. The portions 50 and 52 can be attached to portion 54 by conventional means, or they can be independent of portion 54, e.g. merely laid adjacent and along the sides of a beach towel by the person 46.

It can therefore be seen that the tanning blanket of the present invention not only increases the percentage of the available solar radiation which is directed toward the person utilizing the blanket, it is also capable of distributing this reflected radiation across the flanks of the person to produce a more even tan. It can also be made to selectively absorb a large portion of the sun burning ultraviolet B radiation.

Having thus described several embodiments of the present invention, it will be understood that changes may be made in the size, shape, or configuration of some of the elements described herein without departing from the present invention as recited in the appended claims.

We claim:

1. A tanning blanket for reflecting incident solar radiation toward a person utilizing said blanket, comprising a flexible substrate including a plurality of elongate facets having a reflective covering thereon, said facets being obliquely oriented to direct incident solar radiation generally toward a focal axis located a predetermined distance above the blanket and approximately midway between two opposing outer edges of the blanket.

2. A blanket as claimed in claim 1 further comprising an ultraviolet radiation transparent top layer having a surface covering said facets and conforming thereto.

3. A blanket as claimed in claim 1 or 2 wherein the surface of said facets having the reflective covering thereon is curved in order to slightly disperse the incident solar radiation about said focal axis.

4. A blanket as claimed in claim 1 or 2 wherein said facets vary in the angle they make with respect to an imaginary base line connecting the edges of adjacent facets which edges are most distant from the outer edges of the blanket, and furthermore wherein this angle increases progressively the closer a facet is to the outer edges of said blanket.

5. A blanket as claimed in claim 2 wherein said top layer is transparent to radiation having a wavelength conducive to sun tanning, and absorptive to radiation having a wavelength conducive to sunburning.

6. A blanket as claimed in claim 5 wherein the surface of said facets having the reflective covering thereon is curved in order to slightly disperse the incident solar radiation about said focal axis.

7. A blanket as claimed in claim 5 wherein said facets vary in the angle they make with respect to an imaginary base line connecting the edges of adjacent facets, that are most distant from the outer edges of the blanket, and furthermore wherein this angle increases progressively the closer a facet is to the outer edges of said blanket.

* * * * *